United States Patent [19]

Shoji et al.

[11] Patent Number: 5,268,461
[45] Date of Patent: Dec. 7, 1993

[54] ALKYLATED OLIGOSACCHARIDES AND ACETYL DERIVATIVES OF THE SAME

[75] Inventors: Tadao Shoji, Sakura; Nahoko Takahashi, Chiba; Koichiro Adachi, Kashiwa; Naoya Ikushima; Kaname Katsuraya, both of Sakura; Toshiyuki Uryu; Takashi Yoshida, both of Tokyo, all of Japan

[73] Assignee: Dainippon Ink & Chemicals, Inc., Tokyo, Japan

[21] Appl. No.: 834,305

[22] PCT Filed: Jun. 27, 1991

[86] PCT No.: PCT/JP91/00867
§ 371 Date: Feb. 25, 1992
§ 102(e) Date: Feb. 25, 1992

[87] PCT Pub. No.: WO92/00310
PCT Pub. Date: Jan. 9, 1992

[30] Foreign Application Priority Data

Jun. 27, 1990 [JP] Japan ................... 2-169551
Jun. 27, 1990 [JP] Japan ................... 2-169552
Jul. 31, 1990 [JP] Japan ................... 2-203719

[51] Int. Cl.$^5$ .............. C07H 3/06; C07H 13/06; C07H 15/04
[52] U.S. Cl. .............. 536/41; 536/18.5; 536/18.6; 536/123; 536/123.1; 536/123.13; 536/124
[58] Field of Search ............ 536/4.1, 18.5, 18.6, 536/123, 123.1, 123.13, 124

[56] References Cited

U.S. PATENT DOCUMENTS

| | | | |
|---|---|---|---|
| 3,723,617 | 3/1973 | Sutton | 536/17.5 |
| 4,710,491 | 12/1987 | Lockhoff et al. | 536/22 |
| 4,803,263 | 2/1989 | Thiem et al. | 536/18.6 |
| 4,840,815 | 6/1989 | Meyer et al. | 536/4.1 |
| 4,866,165 | 9/1989 | Lüders | 536/18.5 |
| 4,874,852 | 10/1989 | Kinomura et al. | 536/18.5 |
| 4,889,651 | 12/1989 | Broze | 536/18.6 |
| 4,939,245 | 7/1990 | Rasche et al. | 536/18.5 |
| 4,959,459 | 9/1990 | David et al. | 536/18.5 |
| 4,980,462 | 12/1990 | Karlsson et al. | 514/53 |
| 4,990,605 | 2/1991 | Lueders | 536/18.5 |
| 5,138,046 | 8/1992 | Wuest et al. | 536/18.5 |

FOREIGN PATENT DOCUMENTS

| | | |
|---|---|---|
| 0176118 | 4/1986 | European Pat. Off. |
| 0249013 | 12/1987 | European Pat. Off. |
| 0263027 | 4/1988 | European Pat. Off. |
| 60-251896 | 12/1985 | Japan . |
| 01283294 | 11/1989 | Japan . |
| 0279992 | 3/1990 | Japan . |

*Primary Examiner*—Ronald W. Griffin
*Attorney, Agent, or Firm*—Oblon, Spivak, McClelland, Maier & Neustadt

[57] ABSTRACT

An alkylated oligosaccharide and the acetyl derivative of the same, both useful as the raw material for producing lowly toxic surfactants or medicines. The alkylated oligosaccharide is prepared by substituting with an alkyl group having a linear or branched chain the hydrogen atom of the hydroxy group at the 1-position of a terminal sugar moiety of an oligosaccharide in which glucose moieties are $\beta(1\rightarrow3)$-glucoside-linked, or of an oligosaccharide in which galactose is $\beta(1\rightarrow4)$-glycoside-linked at the 4-position in the galactose moiety of lactose and in which galactose moieties are $\beta(1\rightarrow4)$-glycoside-linked in succession to the newly formed terminal galactose moieties. The invention also includes an acetyl derivative of the oligosaccharide, wherein the hydroxy groups excluding the 2-positional hydroxy group adjacent to the alkyl-ether-linking position in the terminal sugar moiety are acetylated, and a mixture thereof. In addition, an acetylated oligosaccharide is allowed to react with an alcohol using a heteropolyacid as the reacting agent.

9 Claims, No Drawings

ALKYLATED OLIGOSACCHARIDES AND ACETYL DERIVATIVES OF THE SAME

FIELD OF THE INVENTION

The present invention pertains to alkylated oligosaccharides, and more particularly, to alkyl-etherificated oligosaccharides wherein the hydroxy group located at the 1-position in the terminal sugar moiety of the oligosaccharide is alkyl-etherificated. The present invention also relates to alkylated oligosaccharides and the acetyl derivatives of the same which are useful as the raw material for producing lowly toxic surfactants or medicines.

BACKGROUND OF THE INVENTION

Heretofore, it has been known that alkylated sugars are useful as surfactants, and for this reason, the sugars employed as the raw materials have been limited to inexpensive ones. The prior art documents related to the alkylated sugars include: U.S. Pat. No. 3,219,656; U.S. Pat. No. 3,547,828; U.S. Pat. No. 3,839,318; Japanese Pat. Application First Publication No. 58-194901; B. W. LEW et al, J. Am. Oil. Chem. Soc. vol. 47, 163-167 (1970); and the like. These prior art documents pertain to glycosides which are products obtained from reactions between monosaccharides and alcohols. In these prior art documents, although it is disclosed that a small amount of the products obtained from the reactions between the alcohols and the oligosaccharide mainly produced by self-polymerization-reacting the sugars is by-produced, there are no descriptions about the structures, and stereo-and regio- chemistries of the by-product oligosaccharides.

In addition, the oligosaccharides employed as the raw materials of the present invention can be produced by various conventional methods for manufacturing the same. For example, $\beta(1\rightarrow 3)$ oligoglucose can be produced by decomposition of curdlan, laminarane or the like using the enzyme produced by microorganism belonging to the group Streptomyces, or by acid decomposition of curdlan, laminarane or the like.

In addition, a galactose type oligosaccharide having a lactose moiety, $\beta$-D-galactosyl-$\beta(1\rightarrow 4)$-D-galactosyl-$\beta(1\rightarrow 4)$-D-glucose can be produced by the method disclosed in A. Ballio et al. (Tetrahedron, 9, 125, 1960), J. H. Pazur et al. (J. Am. Chem. Soc., 80, 119, 1958), J. G. Collins et al. (Carbohydr. Res., 92, 136, 1981), or Japanese Pat. Application First Publication No. 2-79992 filed by the present applicants. In addition, $\beta$-D-galactosyl-$\beta(1\rightarrow 4)$-D-galactosyl-$\beta(1\rightarrow 4)$-D-galactosyl-$\beta(1\rightarrow 4)$-D-glucose and the like can be produced by the methods disclosed in Japanese Patent Application First Publication No. 60-251896 filed by the present applicants.

However, in the documents described above, there is no description of an alkylated oligosaccharide wherein the oligosaccharide described above is alkylated, nor is a method for producing the same disclosed.

In addition, a number of reports have recently been published wherein the polysaccharide sulfates are useful as the medical agents for Acquired Immune Deficiency Syndrome (AIDS). For this reason, the sulfates of polysaccharides have attracted much attention.

However, these polysaccharides have several disadvantages. They have a strong tendency to act as an anticoagulant, and are difficult to administer due to their poor absorption within a living organism because of molecular weight in excess of ten thousand or more.

It is an object of the present invention to provide a novel alkylated oligosaccharide and the acetyl derivative of the same, having low decomposition properties in a living organism, and which are useful as the raw materials for producing medicines having improved absorption in a living organism.

DESCRIPTION OF THE INVENTION

In order to solve the above described disadvantages of the polysaccharide sulfates, it is an object of the present invention to provide a novel alkylated oligosaccharide and the acetyl derivative of the same having low decomposition-properties in a living organism, improved absorption within a living organism and which are useful as the raw materials for producing medicines.

The alkylated oligosaccharides and the acetyl derivatives of the same according to the present invention are as follows:

1. an alkylated oligosaccharide and the acetyl derivative of the same, wherein the hydrogen atom of the hydroxy group at the 1-position in the terminal sugar moiety of an oligosaccharide in which glucose moieties are $\beta(1\rightarrow 3)$-glycoside-linked, or of an oligosaccharide in which galactose is $\beta(1\rightarrow 4)$-glycoside-linked at the 4-position in the galactose moiety of lactose and in which galactose moieties are $\beta(1\rightarrow 4)$-glycoside-linked in succession to the newly formed terminal galactose moieties, is substituted by an alkyl group having a linear or branched chain;

2. an alkylated oligosaccharide and the acetyl derivative of the same, wherein the hydrogen atom of the hydroxy group at the 1-position in the terminal sugar moiety of an oligosaccharide, in which glucose moieties are $\beta(1\rightarrow 3)$-glycoside-linked, is substituted by an alkyl group having a linear or branched chain;

3. an alkylated oligosaccharide and the acetyl derivative of the same, wherein the hydrogen atom of the hydroxy group at the 1-position in the terminal sugar moiety of an oligosaccharide in which galactose is $\beta(1\rightarrow 4)$-glycoside-linked at the 4-position in the galactose moiety of lactose and in which galactose moieties are $\beta(1\rightarrow 4)$-glycoside-linked in succession to the newly formed terminal galactose moieties, is substituted by an alkyl group having a linear or branched chain;

4. an alkylated oligosaccharide and the acetyl derivative of the same as recited in 2, wherein the oligosaccharide has the glucose moieties in which sugar residues are in the range of 3 to 20;

5. an alkylated oligosaccharide and the acetyl derivative of the same as recited in 3, wherein the oligosaccharide has the galactose moieties in which sugar residues are in the range of 2 to 19 excluding the terminal glucose;

6. an alkylated oligosaccharide and the acetyl derivative of the same as recited in any one of 1 to 5 described above, wherein the alkyl group has a linear or branched chain having 22 or fewer carbon atoms;

7. a mixture including at least two compounds of the alkylated oligosaccharides and the acetyl derivatives of the same as recited in any one of 2 to 6; and 8. an acetyl derivative of an alkylated oligosaccharide, wherein the hydrogen atom of the hydroxy group at the 1-position in the terminal sugar moiety of an oligosaccharide in which glucose moieties are $\beta(1\rightarrow 3)$-glycoside-linked, or of an oligosaccharide in which galactose is β(1→4)-glycoside-linked at the 4-position in the galactose moiety of lactose and in which galactose moieties are β(1→4)-glycoside-linked in succession to the newly formed terminal galactose moieties, is substituted by an alkyl group having a linear or branched chain; and wherein the hydroxy groups excluding the 2-positional hydroxy group adjacent to the alkyl-ether-linking position in the terminal sugar moiety are acetylated.

The above-described alkylated oligosaccharides and the acetyl derivatives of the same according to the present invention have the following effects:

1. Since the oligosaccharide moiety is included in the compounds according to the present invention, the compound has a lower molecular weight in comparison with the conventional polysaccharides. For this reason, the absorption properties are preferably improved in the case where the compounds are used as raw materials of medicines.

2. The compounds according to the present invention have the properties of surfactants since they have both the hydrophilic sugar-chain moieties and such hydrophobic groups as alkyl groups.

In addition, according to the present invention, a method for producing an acetyl derivative of an alkylated oligosaccharide is disclosed, wherein the acetylated oligosaccharide is allowed to react with an alcohol using a heteropolyacid as the reacting agent;

the acetyl derivative of the alkylated oligosaccharide being wherein the hydrogen atom of the hydroxy group at the 1-position in the terminal sugar moiety of an oligosaccharide in which glucose moieties are β(1→3)-glycoside-linked, or of an oligosaccharide in which galactose is β(1→4)-glycoside-linked at the 4-position in the galactose moiety of lactose and in which galactose moieties are β(1→4)-glycoside-linked in succession to the newly formed terminal galactose moieties, is substituted by an alkyl group having a linear or branched chain; and wherein the hydroxy groups excluding the 2-positional hydroxy group adjacent to the alkyl-ether-linking position located in the terminal sugar moiety are acetylated.

In this method, as mentioned above, the acetylated oligosaccharide is allowed to react with an alcohol using a heteropolyacid as a reacting agent. For this reason, it is possible to obtain an oligosaccharide wherein only the 2-positional hydroxy group adjacent to the alkyl-ether-linking position in the terminal sugar is selectively deacetylated.

DETAILED DESCRIPTION OF THE INVENTION

The appropriate sugars employed as raw materials in a method for producing alkylated oligosaccharides and the acetyl derivatives of the same according to the present invention include preferably: lactose derivatives such as three-sugar-linked oligosaccharide wherein galactose is β(1→4)-glycoside-linked at the 4-position in the galactose moiety of lactose, or three to twenty-sugar-linked lactose derivatives wherein galactose moieties are β(1→4)-glycoside-linked in succession to the newly formed terminal galactose moieties of the sugar residues; oligosaccharide compounds having a polymerization degree of 3~20, wherein glucoses are successively β(1→3)-glycoside-linked; and the like. These oligosaccharides can be produced using various methods.

In the method for producing an alkylated oligosaccharide and the acetyl derivative of the same according to the present invention, the oligosaccharide described above is allowed to react with an alcohol to obtain an alkylated glycoside peracetate. Next, the alkylated glycoside peracetate is deacetylated according to the conventional method to obtain an alkylated oligosaccharide.

Thus, an alkylated oligosaccharide and the acetyl derivative of the same according to the present invention can be obtained, wherein the hydrogen atom of the hydroxy group at the 1-position in the terminal sugar moiety of an oligosaccharide in which glucose moieties are β(1→3)-glycoside-linked, or of an oligosaccharide in which galactose is β(1→4)-glycoside-linked at the 4-position in the galactose moiety of lactose and in which galactose moieties are β(1→4)-glycoside-linked in succession to the newly formed terminal galactose moieties, is substituted by an alkyl group having a linear or branched chain, is substituted by an alkyl group having a linear or branched chain.

Reacting the acetylated oligosaccharide with the alcohol in the presence of a heteropolyacid as the reacting agent, the acetyl derivative of the alkylated oligosaccharide wherein one of the acetyl groups of the sugar is selectively deacetylated can be obtained.

In other words, an oligosaccharide wherein only the 2-positional hydroxy group adjacent to the alkyl-ether-linking position in the terminal sugar moiety is selectively deacetylated can be obtained using the method according to the present invention. Heretofore, a method for deacetylating selectively one of the acetyl moieties in an acetylated oligosaccharide has been extremely difficult. Such a compound wherein one of the acetyl moieties of an acetylated oligosaccharide is selectively deacetylated has not been known.

These alkylated oligosaccharides and the acetyl derivatives of the same have surfactive properties. These compounds are useful not only as a surfactant having a low toxicity to creatures, but also for a novel raw material for a medicine.

In addition, the alkyl groups of the alkylated oligosaccharides and the acetyl derivatives thereof according to the present invention have the linear or branched chains having 1 to 22 carbon atoms.

The linking position of the alkyl group of the alkylated sugar according to the present invention is the only reactive point in the oligosaccharide under an acidic condition. In other words, the linking position is at the hydroxy group located at the 1-position in the terminal sugar moiety of the oligosaccharide. Therefore, the alkyl group is inserted at the anomer position. The compound according to the present invention has a glycoside skeleton. (The alkyl-insertion reaction cannot be carried out under the basic conditions.)

Hereinafter, the alkylated oligosaccharides and the acetyl derivatives of the same according to the present invention are listed.

n-butyl β-D-glucopyranosyl-(1→3)-β-D-glucopyranosyl-(1→3)-β-D-glucopyranoside;
n-pentyl β-D-glucopyranosyl-(1→3)-β-D-glucopyranosyl(1→3)-β-D-glucopyranoside;
n-heptyl β-D-glucopyranosyl-(1→3)-β-D-glucopyranosyl(1→3)-β-D-glucopyranoside;
n-octyl β-D-glucopyranosyl-(1→3)-β-D-glucopyranosyl-(1→3)-β-D-glucopyranoside;
n-nonyl β-D-glucopyranosyl-(1→3)-β-D-glucopyranosyl-(1→3)-β-D-glucopyranoside;

n-decyl β-D-glucopyranosyl-(1→3)-β-D-glucopyranosyl-(1→3)-β-D-glucopyranoside;

n-undecyl β-D-glucopyranosyl-(1→3)-β-D-glucopyranosyl-(1→3)-β-D-glucopyranoside;

n-dodecyl β-D-glucopyranosyl-(1→3)-β-D-glucopyranosyl-(1→3)-β-D-glucopyranoside;

n-tetradecyl β-D-glucopyranosyl-(1→3)-β-D-glucopyranosyl-(1→4)-β-D-glucopyranoside;

n-hexadecyl β-D-glucopyranosyl-(1→3)-β-D-glucopyranosyl-(1→3)-β-D-glucopyranoside;

n-octadecyl β-D-glucopyranosyl-(1→3)-β-D-glucopyranosyl-(1→3)-β-D-glucopyranoside;

n-eicosanyl β-D-glucopyranosyl-(1→3)-β-D-glucopyranosyl-(1→3)-β-D-glucopyranoside;

n-docosanyl β-D-glucopyranosyl-(1→3)-β-D-glucopyranosyl-(1→3)-β-D-glucopyranoside;

n-butyl β-D-glucopyranosyl-(1→3)-β-D-glucopyranosyl-β-D-glucopyranosyl-(1→3)-β-D-glucopyranoside;

n-pentyl β-D-glucopyranosyl-(1→3)-β-D-glucopyranosyl(1→3)-β-D-glucopyranosyl-(1→3)-β-D-glucopyranoside;

n-heptyl β-D-glucopyranosyl-(1→3)-β-D-glucopyranosyl(1→3)-β-D glucopyranosyl-(1→3)-β-D-glucopyranoside;

n-octyl β-D-glucopyranosyl-(1→3)-β-D-glucopyranosyl(1→3)-β-D-glucopyranosyl-(1→3)-β-D glucopyranoside;

n-nonyl β-D-glucopyranosyl-(1→3)-β-D-glucopyranosyl(1→3)-β-D-glucopyranosyl-(1→3)-β-D glucopyranoside;

n-decyl β-D-glucopyranosyl-(1→3)-β-D-glucopyranosyl(1→3)-β-D-glucopyranosyl-(1→3)-β-D-glucopyranoside;

n-undecyl β-D-glucopyranosyl-(1→3)-β-D-glucopyranosyl-(1→3)-β-D-glucopyranosyl-(1→3)-β-D-glucopyranoside;

n-dodecyl β-D-glucopyranosyl-(1→3)-β-D-glucopyranosyl-(1→3)-β-D-glucopyranosyl-(1→3)-β-D-glucopyranoside;

n-tetradecyl β-D-glucopyranosyl-(1→3)-β-D-glucopyranosyl-(1→3)-β-D-glucopyranosyl-(1→3)-β-D-glucopyranoside;

n-hexadecyl β-D-glucopyranosyl-(1→3)-β-D-glucopyranosyl-(1→3)-β-D-glucopyranosyl-(1→3)-β-Dglucopyranoside;

n-octadecyl β-D-glucopyranosyl-(1→3)-β-D-glucopyranosyl-(1→3)-β-D-glucopyranosyl-(1→3)-β-Dglucopyranoside;

n-eicosanyl β-D-glucopyranosyl-(1→3)-β-D-glucopyranosyl-(1→3)-β-D-glucopyranosyl-(1→3)-β-D-glucopyranoside;

n-docosanyl β-D-glucopyranosyl-(1→3)-β-D-glucopyranosyl-(1→3)-β-D-glucopyranosyl-(1→3)-β-D-glucopyranoside;

n-butyl β-D-glucopyranosyl-(1→3)-β-D glucopyranosyl-(1→3)-β-D-glucopyranosyl-(1→3)-β-D-glucopyranoside;

n-pentyl β-D-glucopyranosyl-(1→3)-β-D-glucopyranosyl-(1→3)-β-D-glucopyranosyl-(1→3)-β-D-glucopyranosyl-(1→3)-β-D-glucopyranoside;

n-heptyl β-D-glucopyranosyl-(1→3)-β-D-glucopyranosyl-(1→3)-β-D-glucopyranosyl-(1→3)-β-D-glucopyranosyl-(1→3)-β-D-glucopyranoside;

n-octyl β-D-glucopyranosyl-(1→3)-β-D-glucopyranosyl-(1→3)-β-D-glucopyranosyl-(1→3)-β-D glucopyranosyl-(1→3)-β-D-glucopyranoside;

n-nonyl β-D-glucopyranosyl-(1→3)-β-D-glucopyranosyl(1→3)-β-D-glucopyranosyl-(1→3)-β-D-glucopyranosyl-(1→3)-β-D-glucopyranoside;

n-decyl β-D-glucopyranosyl-(1→3)-β-D-glucopyranosyl-(1→3)-β-D-glucopyranosyl-(1→3)-β-D-glucopyranosyl-(1→3)-β-D-glucopyranoside;

n-undecyl β-D-glucopyranosyl-(1→3)-β-D-glucopyranosyl-(1→3)-β-D-glucopyranosyl-(1→3)-β-D-glucopyranosyl-(1→3)-β-D-glucopyranoside;

n-dodecyl β-D-glucopyranosyl-(1→3)-β-D-glucopyranosyl-(1→3)-β-D-glucopyranosyl-(1→3)-β-D-glucopyranosyl-(1→3)-β-D-glucopyranoside;

n-tetradecyl β-D-glucopyranosyl-(1→3)-β-D-glucopyranosyl-(1→3)-β-D-glucopyranosyl-(1→3)-β-D-glucopyranosyl-(1→3)-β-D-glucopyranoside;

n-hexadecyl β-D-glucopyranosyl-(1→3)-β-D-glucopyranosyl-(1→3)-β-D-glucopyranosyl-(1→3)-β-D-glucopyranosyl-(1→3)-β-D-glucopyranoside;

n-octadecyl β-D-glucopyranosyl-(1→3)-β-D-glucopyranosyl-(1→3)-β-D-glucopyranosyl-(1→3)-β-D-glucopyranosyl-(1→3)-β-D-glucopyranoside;

n-eicosanyl β-D-glucopyranosyl-(1→3)-β-D-glucopyranosyl-(1→3)-β-D-glucopyranosyl-(1→3)-→-D-glucopyranosyl-(1→3)-β-D-glucopyranoside;

n-docosanyl B-D-glucopyranosyl-(1→3)-β-D-glucopyranosyl-(1→3)-β-D-glucopyranosyl-(1→3)-β-D-glucopyranosyl-(1→3)-β-D-glucopyranoside;

n-butyl β-D-glucopyranosyl-{(1→3)-β-D-glucopyranosyl}$_m$-(1→3)-β-D-glucopyranoside;

n-pentyl β-D-glucopyranosyl-{(1→3)-β-D-glucopyranosyl}$_m$-(1→3)-β-D-glucopyranoside;

n-heptyl β-D-glucopyranosyl-{(1→3)-β-D-glucopyranosyl}$_m$-(1→3)-β-D-glucopyranoside;

n-octyl β-D-glucopyranosyl-{(1→3)-β-D-glucopyranosyl}$_m$-(1→3)-β-D-glucopyranoside;

n-nonyl β-D-glucopyranosyl-{(1→3)-β-D-glucopyranosyl}$_m$-(1→3)-β-D-glucopyranoside;

n-decyl β-D-glucopyranosyl-{(1→3)-β-D-glucopyranosyl}$_m$-(1→3)-β-D-glucopyranoside;

n-undecyl β-D-glucopyranosyl-{(1→3)-β-D-glucopyranosyl}$_m$-(1→3)-β-D-glucopyranoside;

n-dodecyl β-D-glucopyranosyl-{(1→3)-β-D-glucopyranosyl}$_m$-(1→3)-β-D-glucopyranoside;

n-tetradecyl β-D-glucopyranosyl-{(1→3)-β-D-glucopyranosyl}$_m$-(1→3)-β-D-glucopyranoside;

n-hexadecyl β-D-glucopyranosyl-{(1→3)-β-D-glucopyranosyl}$_m$-(1→3)-β-D-glucopyranoside;

n-octadecyl β-D-glucopyranosyl-{(1→3)-β-D-glucopyranosyl}$_m$-(1→3)-β-D-glucopyranoside;

n-eicosanyl β-D-glucopyranosyl-{(1→3)-β-D-glucopyranosyl}$_m$-(1→3)-β-D-glucopyranoside; and n-docosanyl β-D-glucopyranosyl-{(1→3)-β-D-glucopyranosyl}$_m$-(1→3)-β-D-glucopyranoside.

The compounds listed above are alkylated oligosaccharides. "m" described above represents an integer in the range of 4 to 18.

In addition, the following acetyl derivatives of the compounds listed above are also included in the present invention.

n-butyl β-D-galactopyranosyl-(1→4)-β-D-galactopyranosyl-(1→4)-β-D-glucopyranoside;

n-pentyl β-D-galactopyranosyl-(1→4)-β-D-galactopyranosyl-(1→4)-β-D-glucopyranoside;

n-hexyl β-D-galactopyranosyl-(1→4)-β-D-galactopyranosyl-(1→4)-β-D-glucopyranoside;

n-heptyl β-D-galactopyranosyl-(1→4)-β-D-galactopyranosyl-(1→4)-β-D-glucopyranoside;

n-octyl β-D-galactopyranosyl-(1→4)-β-D-galactopyranosyl-(1→4)-β-D-glucopyranoside;
n-nonyl β-D-galactopyranosyl-(1→4)-β-D-galactopyranosyl-(1→4)-β-D-glucopyranoside;
n-decyl β-D-galactopyranosyl-(1→4)-β-D-galactopyranosyl-(1→4)-β-D-glucopyranoside;
n-undecyl β-D-galactopyranosyl-(1→4)-β-D-galactopyranosyl-(1→4)-β-D glucopyranoside;
n-dodecyl β-D-galactopyranosyl-(1→4)-β-D-galactopyranosyl-(1→4)-β-D-glucopyranoside;
n-tetradecyl B-D-galactopyranosyl-(1→4)-β-D-galactopyranosyl-(1→4)-β-D-glucopyranoside;
n-hexadecyl β-D-galactopyranosyl-(1→4)-β-D-galactopyranosyl-(1→4)-β-D-glucopyranoside;
n-octadecyl β-D-galactopyranosyl-(1→4)-β-D-galactopyranosyl-(1→4)-β-D-glucopyranoside;
n-eicosanyl β-D-galactopyranosyl-(1→4)-β-D-galactopyranosyl-(1→4)-β-D-glucopyranoside;
n-docosanyl β-D-galactopyranosyl-(1→4)-β-D-galactopyranosyl-(1→4)-β-D glucopyranoside;
n-butyl β-D-galactopyranosyl-(1→4)-β-D-galactopyranosyl-(1→4)-β-D-galactopyranosyl-(1→4)-β-D-glucopyranoside;
n-pentyl β-D-galactopyranosyl-(1→4)-β-D-galactopyranosyl-(1→4)-β-D-galactopyranosyl-(1→4)-β-D-glucopyranoside;
n-hexyl β-D-galactopyranosyl-(1→4)-β-D-galactopyranosyl-(1→4)-β-D-galactopyranosyl-(1→4)-β-D-glucopyranoside;
n-heptyl β-D-galactopyranosyl-(1→4)-β-D-galactopyranosyl-(1→4)-β-D-galactopyranosyl-(1→4)-β-D-glucopyranoside;
n-octyl β-D-galactopyranosyl-(1→4)-β-D-galactopyranosyl-(1→4)-β-D-galactopyranosyl-(1→4)-β-D-glucopyranoside;
n-nonyl β-D-galactopyranosyl-(1→4)-β-D-galactopyranosyl-(1→4)-β-D-galactopyranosyl-(1→4)-β-D-glucopyranoside;
n-decyl β-D-galactopyranosyl-(1→4)-βgalactopyranosyl-(1→4)-β-D-galactopyranosyl-(1→4)-β-D-glucopyranoside;
n-undecyl β-D-galactopyranosyl-(1→4)-β-D-galactopyranosyl-(1→4)-β-D-galactopyranosyl-(1→4)-β-D-glucopyranoside;
n-dodecyl β-D-galactopyranosyl-(1→4)-β-D-galactopyranosyl-(1→4)-β-D-galactopyranosyl-(1→4)-β-D-glucopyranoside;
n-tetradecyl β-D-galactopyranosyl-(1→4)-β-D-galactopyranosyl-(1→4)-β-D-galactopyranosyl-(1→4)-β-D-glucopyranoside;
n-hexadecyl β-D-galactopyranosyl-(1→4)-β-D-galactopyranosyl-(1→4)-β-D-galactopyranosyl-(1→4)-β-D-glucopyranoside;
n-octadecyl β-D-galactopyranosyl-(1→4)-β-D-galactopyranosyl-(1→4)-β-D-galactopyranosyl-(1→4)-β-D-glucopyranoside;
n-eicosanyl β-D-galactopyranosyl-(1→4)-β-D-galactopyranosyl-(1→4)-β-D-galactopyranosyl-(1→4)-β-D-glucopyranoside;
n-docosanyl β-D-galactopyranosyl-(1→4)-β-D-galactopyranosyl-(1→4)-β-D-galactopyranosyl-(1→4)-β-D-glucopyranoside;
n-butyl β-D-galactopyranosyl-(1→4)-β-D-galactopyranosyl-(1→4)-β-D-galactopyranosyl-(1→4)-β-D-galactopyranosyl-(1→4)-β-D-glucopyranoside;
n-pentyl β-D-galactopyranosyl-(1→4)-β-D-galactopyranosyl-(1→4)-β-D-galactopyranosyl-(1→4)-β-D-galactopyranosyl-(1→4)-β-D-glucopyranoside;
n-hexyl β-D-galactopyranosyl-(1→4)-βgalactopyranosyl-(1→4)-β-D-galactopyranosyl-(1→4)-β-D-galactopyranosyl-(1→4)-β-D-glucopyranoside;
n-heptyl β-D-galactopyranosyl-(1→4)-β-D-galactopyranosyl-(1→4)-β-D-galactopyranosyl-(1→4)-β-D-galactopyranosyl-(1→4)-β-D-glucopyranoside;
n-octyl β-D-galactopyranosyl-(1→4)-β-D-galactopyranosyl-(1→4)-β-D-galactopyranosyl-(1→4)-β-D-galactopyranosyl-(1→4)-β-D-glucopyranoside;
n-nonyl β-D-galactopyranosyl-(1→4)-β-D-galactopyranosyl-(1→4)-β-D-galactopyranosyl-(1→4)-β-D-glucopyranoside;
n-decyl β-D-galactopyranosyl-(1→4)-β-D-galactopyranosyl-(1→4)-β-D-galactopyranosyl-(1→4)-β-D-galactopyranosyl-(1→4)-β-D-glucopyranoside;
n-undecyl β-D-galactopyranosyl (1→4)-β-D-galactopyranosyl-(1→4)-β-D-galactopyranosyl-(1→4)-β-D-galactopyranosyl-(1→4)-β-D-glucopyranoside;
n-dodecyl β-D-galactopyranosyl-(1→4)-β-D-galactopyranosyl (1→4)-β-D-galactopyranosyl-(1→4)-β-D-galactopyranosyl-(1→4)-β-D-glucopyranoside;
n-tetradecyl β-D-galactopyranosyl-(1→4)-β-D-galactopyranosyl-(1→4)-β-D-galactopyranosyl-(1→4)-β-D-galactopyranosyl-(1→4)-β-D-glucopyranoside;
n-hexadecyl β-D-galactopyranosyl-(1→4)-β-D-galactopyranosyl-(1→4)-β-D-galactopyranosyl-(1→4)-β-D-galactopyranosyl-(1→4)-β-D-glucopyranoside;
n-octadecyl β-D-galactopyranosyl-(1→4)-β-D-galactopyranosyl-(1→4)-β-D-galactopyranosyl-(1→4)-β-D-galactopyranosyl-(1→4)-β-D-glucopyranoside;
n-eicosanyl β-D-galactopyranosyl-(1→4)-β-D-galactopyranosyl-(1→4)-β-D-galactopyranosyl-(1→4)-β-D-galactopyranosyl-(1→4)-β-D-glucopyranoside;
n-docosanyl β-D-galactopyranosyl-(1→4)-β-D-galactopyranosyl-(1→4)-β-D-galactopyranosyl-(1→4)-β-D-galactopyranosyl-(1→4)-β-D-glucopyranoside;
n-butyl β-D-galactopyranosyl-(1→4)-{β-D-galactopyranosyl-(1→4)}$_m$-β-D-glucopyranoside;
n-pentyl β-D-galactopyranosyl-(1→4)-{β-D-galactopyranosyl-(1→4)}$_m$-β-D-glucopyranoside;
n-hexyl β-D-galactopyranosyl-(1→4)-{β-D-galactopyranosyl-(1→4)}$_m$-β-D-glucopyranoside;
n-heptyl β-D-galactopyranosyl-(1→4)-{(β-D-galactopyranosyl-(1→4)}$_m$-β-D-glucopyranoside;
n-octyl β-D-galactopyranosyl-(1→4)-{(β-D-galactopyranosyl-(1→4)}$_m$-β-D-glucopyranoside;
n-decyl β-D-galactopyranosyl-(1→4)-{(β-D-galactopyranosyl-(1→4)}$_m$-β-D-glucopyranoside;
n-undecyl β-D-galactopyranosyl-(1→4)-{(β-D-galactopyranosyl-(1→4)}$_m$-glucopyranoside;
n-dodecyl β-D-galactopyranosyl-(1→4)-{β-D-galactopyranosyl-(1→4)}$_m$-β-D-glucopyranoside;
n-tetradecyl β-D-galactopyranosyl-(1→4)-{β-D-galactopyranosyl-(1→4)}$_m$-β-D-glucopyranoside;
n-hexadecyl β-D-galactopyranosyl-(1→4)-{β-D-galactopyranosyl-(1→4)}$_m$-β-D-glucopyranoside;
n-octadecyl β-D-galactopyranosyl-(1→4)-{β-D-galactopyranosyl-(1→4)}$_m$-β-D-glucopyranoside;
n-eicosanyl β-D-galactopyranosyl-(1→4)-{β-D-galactopyranosyl-(1→4)}$_m$-β-D-glucopyranoside; and
n-docosanyl β-D-galactopyranosyl-(1→4)-{β-D-galactopyranosyl-(1→4)}$_m$-β-D-glucopyranoside.

"m" described in the above listed compound represents an integer in the range of 4 to 18.

In addition, the acetyl derivatives of the compounds listed above, wherein the hydroxy groups in the compounds are acetylated, are included in the present invention. For example, in the acetyl compounds listed above, the example compounds, in which only the 2- positional hydroxy groups adjacent to the linking positions of the alkyl groups are deacetylated, correspond to the compounds in which the hydroxy groups are located at the 2-positions in the terminal sugars.

In addition, the mixtures of the compounds listed above are also included in the present invention.

Next, the method for producing alkylated oligosaccharides and the acetyl derivatives of the same according to the present invention will be explained. The method for producing an alkylated oligosaccharide and the acetyl derivative of the same according to the present invention comprises the steps of: acetylating an oligosaccharide according to the conventional method to obtain an acetylated oligosaccharide; and allowing the acetylated oligosaccharide to react with an alcohol in the presence of various Lewis acid catalysts or in the presence of a heteropolyacid.

The alcohols employed in the present invention include a primary alcohol having a linear or branched chain including carbon atoms in a range of 1 to 22. For example, the following alcohols can be employed:

methanol; ethanol; n propanol; 2-methylpropanol; 2,2-dimethyl-1-propanol; n-butanol; n-pentanol; 2-methyl-1-butanol; 3-methyl-1-butanol; n-hexanol; 2-methyl-1-pentanol; 3-methyl-1-pentanol; 4-methyl-1-pentanol; 3,3-dimethyl-1-butanol; n-heptanol; 2-methyl-1-pentanol; n-octanol; 2-ethyl-I-hexanol; 3,7-dimethyl-l-octanol; n-nonanol; 6-methyl-1-octanol; n-decanol; n-undecanol; n-dodecanol; n-tridecanol; n-tetradecanol; n-pentadecanol; n-hexadecanol; n-heptadecanol; n-octadecanol; nnonadecanol; n-eicosanol; n-docosanol; and the like.

A detailed description related to the method for producing the compounds according to the present invention will be given. The oligosaccharide is acetylated with a large excess of acetic anhydride in a large excess of pyridine according to the conventional method. The reaction mixture is allowed to stand overnight at room temperature and then concentrated under reduced pressure. Next, the residue is dissolved in an organic solvent which is sparingly miscible with water, such as ethyl acetate, methylene chloride, or the like. An aqueous solution of dilute hydrochloric acid is then added thereto. The organic layer is extracted at low temperature and washed with an aqueous solution of sodium bicarbonate. The washed organic layer is dried over anhydrous sodium sulfate, anhydrous magnesium sulfate, or the like. Then, the dried organic layer is concentrated. The residue is purified by means of recrystalization using ethanol or by means of column chromatography.

As another method for acetylation, oligosaccharide may be acetylated using acetic anhydride and sodium acetate. In the former method using pyridine, a $\beta$-acetate derivative is obtained in the amount of more than another anomer of the peracetate, for example, $\beta$-acetate: $\alpha$-acetate=6:4~7:3. On the other hand, in the latter method using sodium acetate, the $\beta$-acetate can be obtained in an amount of approximately 90% or more, as a major product.

The oligosaccharide peracetate obtained by the procedures described above is allowed to react with an alcohol in the presence of a Lewis acid catalyst, such as iron chloride, tin chloride, zinc chloride, boron trifluoride ether, or the like, or in combination therewith, in a solvent such as toluene, methylene chloride, 1,2-dichloroethylene, or the like. The mixture ratio of the oligosaccharide peracetate, the Lewis acid catalyst, and the alcohol is as follows: the Lewis acid catalyst is employed in the amount of 0.1~2.0 mole equivalents, and preferably in the amount of 0.1~1.0 mole equivalents per 1.0 mole of the oligosaccharide peracetate, while the alcohol is employed in the amount of 1.0~5.0 mole equivalents, and preferably in the amount of 1.0~3.0 mole equivalents per 1.0 mole of the oligosaccharide peracetate. In addition, the oligosaccharide peracetate is allowed to react with the alcohol in the presence of the Lewis acid catalyst in the mixture ratio described above under an inert gas at a temperature of from room temperature to the boiling point of the solvent, with the preferable range being between 20° C.~80° C.

The reaction time depends on the types of oligosaccharides and alcohols. Generally, the reaction is carried out for 2~30 hours, and usually for 3~15 hours.

Next, after the reaction is completed, the reaction mixture is poured into ice water. The organic layer is extracted with a solvent which is slightly soluble in reaction mixture. The extracted organic layer is washed successively with water, an aqueous solution of sodium bicarbonate, and a saturated aqueous solution of sodium chloride. The washed organic layer is dried over magnesium sulfate, anhydrous sodium sulfate, or the like, and then concentrated under reduced pressure to obtain a crude product.

The obtained crude product is purified by column chromatography, and by recrystallization as necessary, to isolate the desired alkylated oligosaccharide peracetate.

The alkylated oligosaccharide obtained according to this Lewis acid method has a compound wherein the glycoside is in a $\beta$-configuration as a major product and an $\alpha$-configurated derivative in a small amount. As the alkylation process described above, a method using trimethylsilyl trifluoromethanesulfonate (TMS triflate) or the like as a reacting reagent can be used instead of the method using the Lewis acid described above. In the case of the method using TMS triflate, the reaction temperature is preferably in the range of room temperature to $-20°$ C. In addition, if a heteropolyacid such as tungstophosphoric acid is used as the reacting catalyst instead of a Lewis acid, an $\beta$ derivative can be obtained as a major product. In addition, in order to produce an acetyl derivative of an alkylated oligosaccharide according to the present invention wherein the hydroxy groups are acetylated, excluding the hydroxy group located at the 2-position adjacent to the alkyl-ether linking position, this heteropolyacid is preferably employed. For example, such acetyl derivatives of the alkylated oligosaccharide can be produced by means of the procedures as described in the Lewis acid method, using tungstophosphoric acid, phosphomolybdate, or the like. The reaction temperature is in the range of 60°~130° C, and preferably in the range of 80°~100° C. The reaction time is preferably in the range of 0.1~4 hours, and more preferably in the range of 0.5~3 hours. The obtained crude product is isolated by column chromatography. Alkylated oligosaccharide peracetate thus obtained is allowed to react with sodium methoxide/methanol solution in a catalytic amount or more, generally for 1 hour~50 hours, usually for 1 hour~24 hours, at room temperature.

Precipitation sometimes occurs in the solvent in the case where the oligosaccharide according to the present invention has approximately more than 6~7 sugar residues. The major product of the precipitation is the deacetylated derivative of the alkylated oligosaccharide.

The rest of the precipitation is the acetyl derivative of the alkylated oligosaccharide which is not completely deacetylated and which has one acetyl group to several acetyl groups in the sugar moiety. It is desirable to complete the reaction, the amount of sodium methoxide in the sodium methoxide/methanol solution is preferably in the range of 0.1~1.0 equivalents per 1.0 equivalent of the acetyl group, and more preferably in the amount of 0.1~0.5 equivalent per 1.0 equivalent of the acetyl group. After the reaction is completed, the sodium ions in the reaction mixture are exchanged with hydrogen ions using a H+ type cation exchange resin in a batch system or a column system. The column eluate, or the solution from which the ion exchange has been removed, is then concentrated and dried up. The obtained solid can be purified by recrystallization or reprecipitation, as necessary.

PREFERRED EMBODIMENTS OF THE PRESENT INVENTION

Hereinbelow, the preferred examples of the present invention will be explained. The examples are not intended in any way to limit the scope of the invention.

In connection with the proton nuclear magnetic resonance spectrum, the chemical shift values (ppm), the integral values (the number of protons), the coupling constants (Hz), and the patterns are shown. With regard to signal patterns, doublet is abbreviated as "d", double doublet is abbreviated as "dd", broad doublet is abbreviated as "bd", triplet is abbreviated as "t", broad triplet is abbreviated as "bt", double triplet is abbreviated as "dt", and octet is abbreviated as "oct".

SYNTHETIC EXAMPLE 1 FOR RAW MATERIAL

Synthesis of
β-D-glucopyranosyl-{(1→3)-β-D-glucopyranosyl}$_3$-(1→3)-β-D-glucose peracetate(β-D-laminaripentaose peracetate 2.12 g of anhydrous sodium acetate and 80 ml of acetic anhydride were put in a three neck flask of 100 ml volume, these three necks being utilized for a condenser tube, a thermometer, and an inlet for solids, and then was heated at a temperature near the boiling point of the solvent.

3.6 g of laminaripentaose was added gradually in small amounts to the mixture and then refluxed for 1 hour. The reaction mixture was poured into 250 g of ice and stirred for 4 hours. The organic layer was extracted with chloroform and then washed successively with an aqueous solution of sodium bicarbonate and a saturated aqueous solution of sodium chloride. The washed organic layer was concentrated. The syrupy residue was dissolved in ethanol and decolored by active carbon. The decolored product was crystallized and recrystallized with a solvent of ethyl acetate/hexane to obtain crystals in the amount of 4.96 g. The results of NMR measurements of the obtained crystals showed a 8/92 ration of α product/βproduct. In addition, the crystals had the specific rotation of: $[\alpha]_D = -44.6°$ (c=1.0/chloroform) (25° C).

EXAMPLE 1

Synthesis of n-dodecyl D-glucosyl-β(1→3)-{D-glucosyl-β(1→3)}$_3$-β-D-glucosideperacetate (n-dodecyl β-D-laminaripentaoside peracetate)

2.0 g of the peracetate obtained in Synthetic Example 1 for the raw material was dissolved in 20 g of toluene. 0.26 g of n-dodecyl alcohol was added to the toluenal solution of the peracetate and then 64 mg of anhydrous ferric chloride was added thereto. The mixture was stirred for 1.5 hours at 90° C. After the reaction mixture was cooled, the cooled mixture was poured into ice water. The organic layer was extracted with ethyl acetate. The extracted organic layer was dried over anhydrous sodium sulfate and then concentrated to obtain an oily product in the amount of 2.2 g. The oily product was purified by column chromatography on silica gel (hexane/ethyl acetate), thus obtaining the desired product, n-dodecyl β-D-laminaripentaoside peracetate in the amount of 1.27 g.

Melting point: 94.1~101.3° C.

Specific rotation: $[\alpha]_D = -52.9°$ (c=1.0/chloroform) (25° C.).

The results obtained from the analysis of a proton nuclear magnetic resonance spectrum (CDCl$_3$) (400 MHz) and the COZY method are shown in the following Table 1.

TABLE 1

Nuclear magnetic resonance spectrum of n-dodecyl peracetyl-β-D-laminaripentaoside (proton) (sugar moiety)

| Proton (sugar ring) | A | B | C | D | E |
|---|---|---|---|---|---|
| H-1 | 4.50 | 4.46 | 4.39 | 4.37 | 4.35 |
| H-2 | 4.89 | 4.83 | 4.83 | 4.88 | 4.95 |
| H-3 | 5.11 | 3.78 | 3.80 | 3.77 | 3.86 |
| H-4 | 5.06 | | 4.87~4.93 | | |
| H-5 | 3.8 | | 3.61~3.71 | | 3.64 |
| H-6 | 4.04 | | 4.03~4.31 | | 4.03 |
| | 4.40 | | | | 4.32 |

(δvalue: each of A to E designates each glucose unit and A ring is the terminal sugar ring located at the opposite side of the dodecyl-glycosidated sugar.)

C-13 nuclear magnetic resonance spectrum (CDCL$_3$)

The results obtained from the analysis of the COZY of C-13 and H-1 are shown in the following Table 2.

TABLE 2

Nuclear magnetic resonance spectrum of n-dodecyl peracetyl-β-D-laminaripentaoside (C-13) (sugar moiety)

| Sugar carbon | Ring | | | | |
|---|---|---|---|---|---|
| | A | B | C | D | E |
| C-1 | 101.05 | 100.52 | 100.62 | 100.80 | 100.74 |
| C-2 | 70.84 | 72.40, 73.10 | | 72.40 | 73.15 |
| C-3 | 72.91 | 78.23, 78.95 | | | 78.23 |
| C-4 | 67.99 | 68.11, 68.38, 68.46 | | | |
| C-5 | 71.78 | 71.65, 71.75 | | | 71.75 |
| C-6 | 61.66 | 61.93, 62.05, 62.28 | | | 62.10 |

(δvalue: each of A to E designates each glucose unit and A ring is the terminal sugar ring located at the opposite side of the dodecylglycosidated sugar.)

EXAMPLE 2

Synthesis of n-dodecyl
β-D-glucopyranosyl-{(1→3)-β-D-glucopyranosyl}$_3$-(1→3)-β-D-glucoside (n-dodecyl β-D-laminaripentaoside 346 mg of n-dodecyl β-D-laminaripentaoside peracetate was dissolved in 60 ml of methanol. 6.0 ml of 0.1N sodium methoxide methanol solution was added to the methanol solution of the peracetate at room temperature and then stirred for 24 hours. A cation exchange resin of hydrogen ion type was added to the reaction mixture and then stirred for 5 hours. The ion exchange resin was removed from the mixture by means of filtration. The filtrate was concentrated under reduced pressure to obtain the desired white powder of n-dodecyl β-D-laminaripentaoside in the amount of 203 mg.

Melting point: 180°~195° C.

Specific rotation: $[\alpha]_D = -12.5°$ (c=1.0/methanol) (40° C.).

Proton nuclear magnetic resonance spectrum (δ value, the number of protons) (d=doublet, coupling constant) (DMSO-d$_6$/D$_2$O) (DMSO, methyl=2.50 ppm basis).

| | |
|---|---|
| 0.85 | 3H |
| 1.20~1.35 | 18H |
| 1.45~1.60 | 2H |
| 3.0~3.76 | 32H |
| 4.19 | 1H (d: 8Hz) |
| 4.35 | 1H (d: 8Hz) |
| 4.43 | 1H (d: 8Hz) |
| 4.50 | 2H (d: 8Hz) |

EXAMPLE 3

Synthesis of n-decyl β-D-glucopyranosyl-{(1→3)-β-D-glucopyranosyl}$_3$-(1→3)-β-D-glucoside peracetate Synthesis of n-decyl β-D-laminaripentaoside peracetate The desired compound was obtained in the amount of 383 mg by repeating the same procedures described in Example 1 except that 0.80 g of D-laminaripentaose peracetate (α/β=28/72) was used instead of the peracetate obtained in Synthetic Example 1 and n-decyl alcohol was used in the amount of 123 mg instead of 0.26 g.

Melting point: 96.5°~99.0° C.

Specific rotation: $[\alpha]_D = -40.7°$ (c=1.0/chloroform) (25° C.).

Proton nuclear magnetic resonance spectrum: the same as described in Example 1 except that the protons of the alkylmethylene moiety in 1.20~1.35 ppm were 14 in number.

EXAMPLE 4

Synthesis of n-decyl β-D-glucopyranosyl-{(1→3)-β-D-glucopyranosyl}$_3$-(1→3)-β-D-glucoside Synthesis of n-decyl β-D-laminaripentaoside The desired compound was obtained in the amount of 115 mg by repeating the same procedures described in Example 2 except that 200 mg of n-decyl β-D-laminaripentaoside peracetate obtained in Example 3 was used instead of n-dodecyl β-D-laminaripentaoside peracetate.

Melting point: 180.9°~184 0° C.

Specific rotation: $[\alpha]_D = -15.4°$ (c=1.0/methanol) (25° C.).

Proton nuclear magnetic resonance spectrum (δvalue, the number of protons) (d=doublet, coupling constant) (DMSO-d$_6$/D$_2$O) (DMSO, methyl=2.50 ppm basis)

| | |
|---|---|
| 0.85 | 3H |
| 1.20~1.30 | 14H |
| 1.45~1.60 | 2H |
| 3.0~3.75 | 32H |
| 4.19 | 1H (d: 8Hz) |
| 4.35 | 1H (d: 8Hz) |
| 4.43 | 1H (d: 8Hz) |
| 4.48 | 1H (d: 8Hz) |
| 4.50 | 2H (d: 8Hz) |

EXAMPLE 5

Synthesis of n-hexadecyl β-D-glucopyranosyl-{(1→3)-β-D-glucopyranosyl}$_3$-(1→3)-β-D-glucoside peracetate Synthesis of n-hexadecyl β-D-laminaripentaoside peracetate The desired compound was synthesized by repeating the same procedures described in Example 1 except that n-hexadecyl alcohol was used instead of n-decyl alcohol.

Melting point: 103.1°~106.5° C.

Specific rotation: $[\alpha]_D = 46.6°$ (c=1.0/chloroform) (25° C.).

Proton nuclear magnetic resonance spectrum (CDCl$_3$): with the exception of the integral value for the alkylmethylene moiety, results identical to those described in Example 1 were obtained.

EXAMPLE 6

Synthesis of n-hexadecyl β-D-glucopyranosyl-{(1→3)-β-D-glucopyranosyl}$_3$-(1→3)-β-D-glucoside Synthesis of n-hexadecyl β-D-laminaripentaoside The desired compound was obtained in the amount of 112 mg by repeating the same procedures described in Example 2 except that 190 mg of the n-hexadecyl β-Dlaminaripentaoside peracetate obtained in Example 5 was used instead of n-dodecyl β-D-laminaripentaoside peracetate.

Melting point: 198.0°~204.1° C.

Specific rotation: $[\alpha]_D = -11.4°$ (c=0.7/methanol) (25° C.).

Proton nuclear magnetic resonance spectrum (DMSO-d6/D20) (DMSO, methyl=2.50 ppm basis): the same as described in Example 4 except that the protons of the alkyl methylene moiety at 1.20~1.35 ppm were 26 in number.

EXAMPLE 7

Synthesis of n-octadecyl β-D-glucopyranosyl-{(1→3)-β-D-glucopyranosyl}$_3$-(1→3)-β-D-glucoside peracetate Synthesis of n-octadecyl β-D-laminaripentaoside peracetate.

The desired compound was synthesized by repeating the same procedures described in Example 1.

Melting point: 90.9°~97.0° C.

Specific rotation: $[\alpha]_D = -50.3°$ (c=1.0/chloroform) (25° C.).

Proton nuclear magnetic resonance spectrum (CDCl$_3$): with the exception of the integral value for the alkylmethylene moiety, results identical to those described in Example were obtained.

EXAMPLE 8

Synthesis of n-octadecyl
β-D-glucopyranosyl-{(1→3)-β-D-glucopyranosyl}₃-
(1→3)-β-D-glucoside (Synthesis of n-octadecyl
β-D-laminaripentaoside The desired compound was obtained using the compound obtained in Example 7 by repeating the same procedures described in Example 2.

Melting point: 228.5°~234.8° C.

Specific rotation: $[\alpha]_D = 14.4°$ (c=1.0/methanol) (25° C.).

Proton nuclear magnetic resonance spectrum (DMSO-d6/D₂O) (DMSO, methyl=2.50 ppm basis): the same as described in Example 2 except that the protons of the alkyl methylene moiety at 1.20~1.35 ppm were 30 in number.

EXAMPLE 9

Synthesis of n-dodecyl
β-D-glucopyranosyl-{(1→3)-β-D-glucopyranosyl}ₘ-
(1→3)-β-D-glucoside peracetate (m=5~18)

Synthesis of n-dodecyl β(1→3) oligoglucoside peracetate 3.17 g of β(1→3) oligoglucose sugar obtained by means of fermentation synthesis (according to analysis by HPLC using TSK Gel Amide 80 column produced by Toso Industries, Co., Ltd., average molecular weight: 1860, including 5~18 sugar residues, content ratio: 2% of 5~7 sugar residues; 81% of 8~14 sugar residues; 17% of 15~18 sugar residues) was acetylated using acetic anhydride and sodium acetate by the conventional method, whereby a peracetyl derivative in the amount of 4.32 g was obtained.

2.02 g of the peracetyl derivative and 0.8 g of n-dodecylalcohol were dissolved in 20 ml of methylene chloride. The solution was reacted in the presence of 0.05 g of tin tetrachloride as a catalyst under an argon atmosphere for 60 hours at 25°-35° C. According to the conventional after-treatment, the reaction mixture was diluted with methylene chloride, and then washed successively with water, an aqueous solution of sodium bicarbonate, and a saturated aqueous solution of sodium chloride. The organic layer was dried over anhydrous sodium sulfate and concentrated under reduced pressure. The residue was purified by column chromatography, whereby a powdery dodecyl either derivative (an acetyl derivative of dodecanol glycoside) was obtained in the amount of 1.7 g.

Specific rotation: $[\alpha]_D = +4.5°$ (c=0.56/chloroform) (27° C.).

Proton nuclear magnetic resonance spectrum (δvalue, the number of protons) (CDCl₃) (TMS=0 ppm basis)

| | |
|---|---|
| 0.85 | 3H (Hereinafter, the integral values were based on this 3H value.) |
| 1.20~1.30 | 18H |
| 1.60~1.75 | 2H |
| 1.9~2.2 | approximately 110H (the acethylmethyl moiety) |
| 3.4~4.95 | approximately 25.7H (3-position and 5-position in the sugar moiety, and α-position in the alkyl moiety) |
| 3.95~4.15 | approximately 11.8H (6-position in the sugar moiety) |
| 4.15~4.6 | approximately 23.7H (6-position and 1-position in the sugar moiety) |
| 4.6~5.05 | approximately 23.7H (2-position and 4-position in the sugar moiety) |
| 5.60 | 1H (3-position in the terminal sugar moiety) |

EXAMPLE 10

Synthesis of n-dodecyl β-D-glucopyranosyl-{(1→3)-β-D-glucopyranosyl}ₘ-(1→3)-β-D-glucoside peracetate (m=5~13)

Synthesis of dodecyl β(1→3) oligoglucoside peracetate
(2)

2.0 g of β(1→3) oligoglucose sugar peracetate synthesized by an acetolysis (acetic anhydride, acetic acid, sulfuric acid process) of curdlan (according to analysis by HPLC using a TSK Gel Amide 80 column produced by Toso Industries, Co., Ltd., average molecular weight after deacetylation: 1610, including 5~13 sugar residues, content ratio: 10% of 5~7 sugar residues; 53% of 8~10 sugar residues; 37% of 11-13 sugar residues), 0.8 g of n-dodecyl alcohol were dissolved in 20 ml of methylene chloride. The solution was reacted in the presence of 0.05 g of tin tetrachloride as a catalyst under an argon atmosphere for 60 hours at 25°~35° C. According to the conventional after-treatment, the reaction mixture was diluted with methylene chloride, and then washed successively with water, an aqueous solution of sodium bicarbonate, and a saturated aqueous solution of sodium chloride. The organic layer was dried over anhydrous sodium sulfate and concentrated under reduced pressure. The residue was purified by column chromatography, whereby a powdery dodecyl ether derivative (acetyl derivative of dodecanol glycoside) was obtained in the amount of 1.53 g.

Specific rotation: $[\alpha]_D = +4.3°$ (c=0.60/CHCl₃) 27° C.

Proton nuclear magnetic resonance spectrum (δvalue, the number of protons) (CDCl₃) (TMS=0 ppm basis)

| | |
|---|---|
| 0.85 | 3H (Hereinafter, the integral values (the number of protons) were based on this 3H value.) |
| 1.20~1.30 | 18H |
| 1.60~1.75 | 2H |
| 1.9~2.2 | approximately 30H (the acethylmethyl moiety) |
| 3.4~4.95 | approximately 21.7H (3-position and 5-position in the sugar moiety, and α-position in the alkyl moiety) |
| 3.95~4.15 | approximately 9.9H (6-position in the sugar moiety) |
| 4.15~4.6 | approximately 19.7H (6-position and 1-position in the sugar moiety) |
| 4.6~5.05 | approximately 19.7H (2-position and 4-position in the sugar moiety) |
| 5.60 | 1H (3-position in the terminal sugar moiety) |

EXAMPLE 11

Synthesis of dodecyl
β(1→3)-β-D-glucopyranosyl}$_m$-(1→3)-β-D-glucoside peracetate (m=8~18)

Synthesis of dodecyl β(1→3) oligoglucoside peracetate (3)

2.0 g of β(1→3)oligoglucose sugar peracetate synthesized by an acetolysis (acetic anhydride, acetic acid, sulfuric acid process) of curdlan (according to analysis by HPLC using a TSK Gel Amide 80 column produced by Toso Industries, Co., Ltd., average molecular weight after deacetylation: 2340, including 8~18 sugar residues, content ratio: 12% of 8~12 sugar residues; 62% of 13~15 sugar residues; 26% of 16~18 sugar residues), 0.8 g of ndodecyl alcohol were dissolved in 20 ml of methylene chloride. The solution was reacted in the presence of 0.05 g of tin tetrachloride as a catalyst under an argon atmosphere for 55 hours at 25°~33° C. According to the conventional after-treatment, the reaction mixture was diluted with methylene chloride, and then washed successively with water, an aqueous solution of sodium bicarbonate, and a saturated aqueous solution of sodium chloride. The organic layer was dried over anhydrous sodium sulfate and concentrated under reduced pressure. The residue was purified by column chromatography, whereby a powdery dodecyl ether derivative (acetyl derivative of dodecanol glycoside) was obtained in the amount of 1.43 g.

Specific rotation: $[\alpha]_D = +4.6°$ (c=0.50/CHCl$_3$) 27° C.

Proton nuclear magnetic resonance spectrum (δ value, the number of protons) (CDCl$_3$) (TMS=0 ppm basis)

| | |
|---|---|
| 0.85 | 3H (Hereinafter, the integral values (the number of protons) were based on this 3H value.) |
| 1.20~1.30 | 18H |
| 1.60~1.75 | 2H |
| 1.9~2.2 | approximately 44H (the acethylmethyl moiety) |
| 3.4~5.05 | approximately 94H (protons of the sugar moiety, and α-position in the alkyl moiety) |
| 5.60 | 1H (3-position in the terminal sugar moiety) |

EXAMPLE 12

Synthesis of n-dodecyl δ-D-glucopyranosyl-{(1→3)-β-D-glucopyranosyl)m-(1→3)-β-D-glucoside (m=5~18)

Synthesis of n-dodecyl β(1→3) oligoglucoside 1.0 g of the dodecyl β(1→3) oligoglucoside peracetate obtained in Example 9 was dissolved in 18 ml of 0.1N sodium methoxide methanol solution. The solution was reacted for 20 hours at room temperature. In addition, a hydrogen ion type cation exchange resin was added to the reaction mixture and then stirred for 5 hours. The solution, from which the ion exchange resin was removed by means of filtration, was concentrated under reduced pressure, whereby the desired n-dodecyl β(1→3) oligoglucoside was obtained in the amount of 0.41 g in the powdery state.

Specific rotation: $[\alpha]_D = +26.5°$ (c=0.52/H$_2$O) 25° C.

Proton nuclear magnetic resonance spectrum (δ value, the number of protons) (DMSO-d6) (DMSO, methyl=2.50 ppm basis)

| | |
|---|---|
| 0.86 | 3H |
| 1.25 | 18H |
| 1.52 | 2H |
| 3.0~3.75 | (the integral value was not able to be determined since there was overlapped absorption of H$_2$O.) (2-position~6-position in the sugar moiety, and the α methylene moiety) |
| 4.2~4.6 | approximately 12H (protons at 1-position in the sugar moiety) |

| | |
|---|---|
| 0.86 | 3H |
| 1.25 | 18H |
| 1.52 | 2H |
| 3.0~3.75 | (the integral value was not able to be determined since there was overlapped absorption of H$_2$O.) (2-position~6-position in the sugar moiety, and the α methylene moiety) |
| 4.2~4.6 | approximately 12H (protons at 1-position in the sugar moiety) |

EXAMPLE 13

Synthesis of n-dodecyl
β-D-glucopyranosyl-{(1→3)-β-D-glucopyranosyl}$_m$-(1→3)-β-D-glucoside (m=5~13)

Synthesis of n-dodecyl β(1→3) oligoglucoside (2)

1.0 g of n-dodecyl β(1→3) oligoglucoside peracetate synthesized according to the procedures described in Example 10 was deacetylated using sodium methoxide/methanol solution as described in Example 12, thereby obtaining the powdered desired product in the amount of 0.41 g.

Specific rotation $[\alpha]_D = +26.0°$ (c=0.50/H$_2$O) 27° C.

Proton nuclear magnetic resonance spectrum (δ value, the number of protons) (DMSO-d$_6$) (DMSO, methyl=2.50 ppm basis)

| | |
|---|---|
| 0.86 | 3H |
| 1.25 | 18H |
| 1.52 | 2H |
| 3.0~3.75 | (the integral value was not able to be determined since there was overlapped absorption of H$_2$O.) (2-position~6-position in the sugar moiety, and the α methylene moiety) |
| 4.2~4.6 | approximately 10H (protons at 1-position in the sugar moiety) |

EXAMPLE 14

Synthesis of n-dodecyl
β-D-glucopyranosyl-{(1→3)-β-D-glucopyranosyl)m-(1→3)-β-D-glucoside (m=8~18)

Synthesis of n-dodecyl β(1Δ3) oligoglucoside (3)

1.0 g of n-dodecyl β(1Δ3) oligoglucoside peracetate synthesized according to the procedures described in Example 11 was deacetylated using sodium methoxide/methanol solution as described in Example 12, thereby obtaining the powdered dodecanol glycoside in the amount of 0.40 g.

Specific rotation: $[\alpha]_D = +26.8°$ (c=0.50/H$_2$O) 27° C.

Proton nuclear magnetic resonance spectrum ($\delta$ value, the number of protons) (DMSO-d$_6$) (DMSO, methyl=2.50 ppm basis)

| | |
|---|---|
| 0.86 | 3H |
| 1.25 | 18H |
| 1.52 | 2H |
| 3.0~3.75 | (the integral value was not able to be determined since there was overlapped absorption of H$_2$O.) (2-position~6-position in the sugar moiety, and the $\alpha$ methylene moiety) |
| 4.2~4.7 | approximately 14H (protons at 1-position in the sugar moiety) |

SYNTHETIC EXAMPLE 2 FOR RAW MATERIAL

Synthesis of undecaacetyl-D-galactosyl-$\beta$\{1→4\}-D-lactose 5.0 g of D-galactosyl-$\beta$(1→4)-D-lactose was acetylated using acetic anhydride and sodium acetate, thus obtaining undecaacetyl-4-galactosyl-D-lactose in the amount of 9.5 g. (composition ratio: $\beta/\alpha = 3.2$)

Specific rotation: $[\alpha]_D = +6.7°$ (c=1.0/CHCl$_3$).

Proton nuclear magnetic resonance spectrum

| | | | |
|---|---|---|---|
| 6.25 | d: 4.0 Hz | glucose | 1-position ($\alpha$) |
| 5.66 | d: 8.0 Hz | glucose | 1-position ($\beta$) |
| 5.30 | bd: 3.2 Hz | terminal galactose | 4-position |

EXAMPLE 15

Synthesis of n-decyl undecaacetyl-D-galactosyl-$\beta$(1→4)-$\beta$-D-lactoside 5.0 g of the acetate obtained in Synthetic Example 2 for the raw material was dissolved in 10 ml of toluene. 0.04 g of tungstophosphoric acid catalyst and 1.0 g of n-decyl alcohol were successively added to the solution and stirred for 5 hours at 100°~105° C. After the reaction mixture was poured into ice water, the organic layer was extracted with ethyl acetate. The ethyl acetate layer was washed successively with an aqueous solution of sodium bicarbonate, and a saturated aqueous solution of sodium chloride. The washed organic layer was dried over anhydrous sodium sulfate and then concentrated under reduced pressure, whereby the residue was obtained in the amount of 6.1 g. The residue was purified by column chromatography on silica gel (hexane/ethyl acetate), thus obtaining the desired $\beta$-glycoside in the amount of 3.85 g in the powdered state.

Specific rotation: $[\alpha]_D = +0.5°$ (c=1.2/CHCl$_3$) 27° C.

Proton nuclear magnetic resonance spectrum (protons/CDCl$_3$) $\delta$ value; coupling constant Hz

| (1) the glucose moiety | | |
|---|---|---|
| C-1 position | 4.44 | J (1, 2) = 8 Hz |
| C-2 position | 4.90 | J (2, 3) = ca. 10 |
| C-3 position | 5.18 | J (3, 4) = ca. 10 |
| C-4 position | 3.78 | J (4, 5) = ca. 10 |
| C-5 position | 3.60 | J (5, 6a) = 4.2 |
| C-6 position | 6a position 4.11; 6b position 4.46 | |
| | | J (5, 6b) = 2.0 |
| | | J (6a, 6b) = 12 |
| (2) the intermediate galactose moiety | | |
| C-1 position | 4.22 | J (1, 2) = 8 Hz |
| C-2 position | 4.98 | J (2, 3) = ca. 10 |
| C-3 position | 4.86 | J (3, 4) = ca. 3.2 |
| C-4 position | 4.10 | J (4, 5) = ca. 0.5 |
| C-5 position | 3.69 | J (5, 6a) = 6.4 |
| C-6 position | 6a position 4.17; 6b position 4.32 | |
| | | J (5, 6b) = 6.4 |
| | | J (6a, 6b) = 12 |
| (3) the terminal galactose moiety | | |
| C-1 position | 4.50 | J (1, 2) = 8 Hz |
| C-2 position | 5.17 | J (2, 3) = ca. 10 |
| C-3 position | 4.99 | J (3, 4) = ca. 3.2 |
| C-4 position | 5.37 | J (4, 5) = ca. 0.5 |
| C-5 position | 3.69 | J (5, 6a) = 6.4 |
| C-6 position | 4.05~4.15 | |
| | | J (5, 6b) = 6.4 |
| | | J (6a, 6b) = 12 |
| alkyl chain $\alpha$-position | 3.45, 1H; 3.82, 1H | |
| acetyl methyl | 1.8~2.1 30H | |
| alkyl chain $\beta$-position | 1.25 2H | |
| alkyl methylene | 1.1~1.4 14H | |
| alkyl chain terminal methyl | 0.88 3H | |

EXAMPLE 16

Synthesis of n-decyl 3,6,2',3',6',2'',4'',6''-nonaacetyl-D-galactosyl-$\beta$(1→4)-$\beta$-D-lactoside A fraction of 0.53 g was obtained from the latter fraction of the column chromatography in Example 15 described above. Through NMR analysis, this product was discovered to be an $\alpha$-glycoside wherein the 2-positional glucose moiety was deacetylated.

Nuclear magnetic resonance spectrum (protons/CDCl$_3$) $\delta$ value; coupling constant Hz

| (1) the glucose moiety | | |
|---|---|---|
| C-1 position | 4.84 | J (1, 2) = 8 Hz |
| C-2 position | 3.55 | J (2, 3) = ca. 10 |
| | | J (2, OH) = ca. 10 |
| C-3 position | 5.21 | J (3, 4) = ca. 10 |
| C-4 position | 3.64 | J (4, 5) = ca. 10 |
| C-5 position | 3.87 | J (5, 6a) = 5.2 |
| C-6 position | 6a position 4.12; 6b position 4.40 | |
| | | J (5, 6b) = 2.0 |
| | | J (6a, 6b) = 12 |
| (2) the intermediate galactose moiety | | |
| C-1 position | 4.43 | J (1, 2) = 8 Hz |
| C-2 position | 4.98 | J (2, 3) = ca. 10 |
| C-3 position | 4.86 | J (3, 4) = ca. 3.2 |
| C-4 position | 4.10 | J (4, 5) = ca. 0.5 |
| C-5 position | 3.68 | J (5, 6a) = ca. 6 |
| C-6 position | 6a position 4.22; 6b position 4.33 | |
| | | J (5, 6b) = ca. 6 |
| | | J (6a, 6b) = 12 |
| (3) the terminal galactose moiety | | |
| C-1 position | 4.50 | J (1, 2) = 8 Hz |
| C-2 position | 5.18 | J (2, 3) = ca. 10 |
| C-3 position | 5.00 | J (3, 4) = ca. 3.2 |
| C-4 position | 5.67 | J (4, 5) = ca. 0.5 |
| C-5 position | 3.83 | J (5, 6a) = ca. 6 |
| C-6 position | 4.05~4.15 | |
| | | J (5, 6b) = ca. 6 |
| | | J (6a, 6b) = 12 |
| alkyl chain $\alpha$-position | 3.44, 1H; 3.69, 1H | |
| acetyl methyl | 1.8~2.1 27H | |
| alkyl chain $\beta$-position | 1.25 2H | |
| alkyl methylene | 1.1~1.4 14H | |
| alkyl chain terminal methyl | 0.88 3H | |

EXAMPLE 17

Synthesis of n-decyl
D-galactosyl-β(1→4)-β-D-lactoside 1.5 g of the peracetate obtained in Example 15 was dissolved in 45 ml of methanol. 15 ml of 0.1N sodium methoxide methanol solution was added to the solution and stirred for 5 hours at room temperature. The insoluble matter in the reaction mixture was removed by filtration. A hydrogen ion type ion exchanger was added to the filtrate and then stirred at room temperature to remove the sodium ions. The ion exchanger was removed by means of filtration. The filtrate was concentrated and then fully dried, thereby obtaining the desired powdery compound in the amount of 0.87 g.

Specific rotation $[\alpha]_D = +51.5°$ (c=1.08/H$_2$O).

Proton nuclear magnetic resonance spectrum (δ value, the number of protons) (CD$_3$OD)

| | |
|---|---|
| 0.90 | 3H |
| 1.20~1.45 | 14H |
| 1.50~1.70 | 2H |
| 3.40~4.76 | 23H |

EXAMPLE 18

Synthesis of n-dodecyl
D-galactosyl-β(1→4)-β-D-lactoside

The same procedures described in Example 15 were carried out except that n-dodecyl alcohol was used instead of the n-decyl alcohol in Example 15, thereby obtaining n-dodecyl D-galactosyl-β(1→4)-β-D-lactoside peracetate. The peracetate obtained above was deacetylated according to the procedures described in Example 17, whereby the desired powdered compound was obtained.

Specific rotation: $[\alpha]_D = +46.4°$ (c=1.10/H$_2$O).

Proton nuclear magnetic resonance spectrum (δ value, the number of protons) (CD$_3$OD)

| | |
|---|---|
| 0.90 | 3H |
| 1.20~1.45 | 18H |
| 1.50~1.70 | 2H |
| 3.40~4.76 | 23H |

EXAMPLE 19

Synthesis of n-octadecyl
D-galactosyl-β(1→4)-β-D-lactoside

The same procedures described in Examples 15 were carried out except that n-octadecyl alcohol was used instead of the n-decyl alcohol in Example 15, thereby obtaining n-octadecyl D-galactosyl-δ(1→4)-δ-D-lactoside peracetate. The peracetate obtained above was deacetylated according to the procedures described in Example 17, whereby the desired powdered compound was obtained.

Specific rotation: $[\alpha]_D = +29.8°$ (C=0.58/H$_2$O).

Proton nuclear magnetic resonance spectrum δ value, the number of protons) (CD$_3$OD)

| | |
|---|---|
| 0.90 | 3H |
| 1.20~1.45 | 30H |
| 1.50~1.70 | 2H |
| 3.40~4.76 | 23H |

EXAMPLE 20

Synthesis of n-dodecyl
D-galactosyl-β(1→4)-D-galactosyl-β(1→4)-β-D-lactoside peracetate 2.8 g of D-galactosyl-β(1→)-D-galactosyl-β(1→4)-D-lactose peracetate was dissolved in 10 ml of methylene chloride. 0.12 ml of tin tetrachloride and 745 mg of n-dodecyl alcohol were successively added to the solution and then stirred for 7.5 hours under an argon atmosphere at room temperature. The reaction mixture was poured into ice water and the organic layer was extracted with ethyl acetate. The ethyl acetate layer was washed successively with an aqueous solution of sodium bicarbonate and a saturated aqueous solution of sodium chloride, and then dried over anhydrous sodium sulfate The organic layer was concentrated under reduced pressure, thereby the residue was obtained in the amount of 3.46 g. The residue was purified by column chromatography on silica gel (hexane/ethyl acetate), thus obtaining the desired powdered (glycoside in the amount of 1.72 g.

Specific rotation: $[\alpha]_D = +13.9°$ (c=1.0/chloroform) 26° C.

Proton nuclear magnetic resonance spectrum (CDCl$_3$)

| | |
|---|---|
| 0.88 | 3H |
| 1.15~1.35 | 18H |
| 1.78 | 2H |
| 1.97~2.17 | 39H |
| 3.44 | 1H (dt: 1H of the methylene moiety adjacent to the oxygen atom) |
| 3.58 | 1H (oct: 5-position in the glucose moiety) |
| 3.64 | 1H (bt: 5-position in the galactose moiety adjacent to the glucose moiety) |
| 3.68 | 1H (bt: 5-position in the second galactose moiety from the glucose) |
| 3.76 | 1H (t: 9.6 Hz/4-position in the glucose moiety) |
| 3.82 | 1H (dt: 1H of the methylene moiety adjacent to the oxygen atom) |
| 3.83 | 1H (bt: 5-position in the terminal galactose moiety) |
| 4.08~4.48 | 14H (each 1-position, each 6-position, and 4-position in the intermediate galactose ) |
| (4.35 = 1H/d: 8 Hz 1-position in the galactose moiety adjacent to the glucose moiety) | |
| (4.42 = 1H/d: 8 Hz 1-position in the glucose moiety) | |
| (4.43 = 1H/d: 8 Hz 1-position in the second galactose moiety from the glucose moiety) | |
| (4.45 = 1H/d: 8 Hz 1-position in the terminal galactose moiety) | |
| 4.83 | 1H (dd: J = 3.2 Hz/10 Hz 3-position in the galactose moiety adjacent to the glucose moiety) |
| 4.88 | 1H (dd: J = 3.2 Hz/10 Hz 3-position in the second galactose moiety from the glucose moiety) |
| 4.90 | 1H (dd: J = 8 Hz/10 Hz 2-position in the glucose moiety) |
| 4.94 | 1H (dd: J = 8 Hz/10 Hz |

| | |
|---|---|
| 5.00 | 2-position in the galactose moiety from the glucose moiety) 1H (dd: J = 3.2 Hz/10 Hz 3-position in the terminal galactose moiety) |
| 5.02 | 1H (dd: J = 8 Hz/10 Hz 2-position in the second galactose moiety from the glucose moiety) |
| 5.16 | 1H (t: J = 10 Hz 3-position in the glucose moiety) |
| 5.19 | 1H (dd: J = 8 Hz/10 Hz 2-position in the terminal galactose moiety) |
| 5.37 | 1H (bd: J = 3.2 Hz 4-position in the terminal galactose moiety) |

EXAMPLE 21

Synthesis of n-dodecyl D-galactosyl-$\beta(1\rightarrow4)$-D-galactosyl-$\beta(1\rightarrow4)$-$\beta$-D-lactoside 1.0 g of the D-galactosyl-$\beta(1\rightarrow4)$-D-galactosyl-$\beta(1\rightarrow4)$-$\beta$-D lactose peracetate obtained in Example 20 was deacetylated as described in Example 17, thereby obtaining the desired powdered n-dodecyl D-galactosyl-$\beta(1\rightarrow4)$-D-galactosyl-$\beta(1\rightarrow4)$-$\beta$-D-lactoside in the amount of 0.48 g.

Specific rotation: $[\alpha]_D = +22.8°$ (c=1.0/methanol) 31° C.

Proton nuclear magnetic resonance spectrum (MeOHd$_4$+D$_2$O)

| | |
|---|---|
| 0.90 | 3H |
| 1.2~1.4 | 18H |
| 1.59~1.64 | 2H |
| 3.2~4.48 | 30H |

(4.27: 1H, 4.37: 1H, 4.45: 1H, 4.47: 1H; J=8Hz for each proton at the anomer position in each sugar)

EXAMPLE 22

Synthesis of n-dodecyl peracetyl-D-galactosyl-$\beta(1\rightarrow4)$-{D-galactosyl-$\beta(1\rightarrow4)$}$_m$-D-lactoside (m=1~2)

3.0 g of D-galactosyl-$\beta(1\rightarrow4)$-{D-galactosyl-$\beta(1\rightarrow4)$}$_m$-D-lactose peracetate (4 sugar rings/5 sugar rings mole ratio of approximately 1/0.5) was dissolved in 20 ml of methylene chloride. 0.19 ml of tin tetrachloride and 790 mg of n-dodecyl alcohol were successively added to the solution and then stirred for 8.5 hours under an argon atmosphere at room temperature. The reaction mixture was poured into ice water. The organic layer was extracted with ethyl acetate. The ethyl acetate layer was washed successively with an aqueous solution of sodium bicarbonate and a saturated solution of sodium chloride, and then dried over anhydrous sodium sulfate. The organic layer was concentrated under reduced pressure, whereby the residue was obtained in the amount of 3.22 g. The residue was purified by column chromatography on silica gel (hexane/ethyl acetate), whereby the desired powdered $\beta$-glycoside was obtained in the amount of 1.62 g.

Specific rotation: $[\alpha]_D = +41.6°$ (c=1.15/chloroform) 27° C.

Proton nuclear magnetic resonance spectrum (CDCl$_3$)

| | |
|---|---|
| 0.88 | 3H (the alkylmethyl moiety) |
| 1.15~1.4 | 18H (the intermediate alkylmethylene moiety) |
| 1.5~1.65 | 2H (the alkoxy $\beta$-position methylene moiety) |
| 1.99~2.22 | 42H (the acetylmethyl moiety) |
| 3.2~5.4 | 32.3H (the sugar ring protons and the alkoxy $\alpha$-position methylene moiety) |

Synthesis of n-dodecyl D-galactosyl-$\beta(1\rightarrow4)$-{D-galactosyl-$\beta(1\rightarrow4)$}$_m$-D-lactoside (m=1~2)

The desired powdered $\beta$-glycoside was obtained by repeating the same procedures as described in Example 17 except that 1.0 g of the D-galactosyl-$\beta(1\rightarrow4)$-{D-galactosyl-$\beta(1\rightarrow4)$}$_m$-D-lactoside peracetate obtained in Example 22 was used instead of the peracetate obtained in Example 15.

Specific rotation: $[\alpha]_D = +46.8°$ (c=0.52/H$_2$O) 27° C.

Proton nuclear magnetic resonance spectrum (MeOH d$_5$)

| | |
|---|---|
| 0.89 | 3H (the alkylmethyl moiety) |
| 1.2~1.4 | 18H (the intermediate alkylmethylene moiety) |
| 1.55~1.65 | 2H (the alkoxy $\beta$-position methylene moiety) |
| 3.2~5.4 | 32.3H (the sugar ring protons and the alkoxy $\alpha$-position methylene moiety) |

POSSIBLE APPLICATION FOR INDUSTRIAL USE

The compounds according to the present invention can be used as raw materials in such fields where there is a need for sugars having a low toxicity, excellent absorption within an organism, and a surfactant activity. Additionally, the compounds according to the present invention may be used as surfactants to be added to medicines or used as raw materials for producing medicines having sugar rings in the molecular structure.

What is claimed is:

1. An alkylated oligosaccharide and the acetyl derivative of the same, wherein the hydrogen atom of the hydroxy group of the 1-position in the terminal sugar moiety of an oligosaccharide in which glucose moieties are $\beta(1\rightarrow3)$-glucoside-linked, or of an oligosaccharide in which galactose is $\beta(1\rightarrow4)$-glycoside-linked at the 4-position in the galactose moiety of lactose and in which galactose moieties are $\beta(1\rightarrow4)$-glycoside-linked in succession to newly formed terminal galactose moieties, is substituted by an alkyl group having a linear or branched chain, with the exception of O-$\beta$-D-galactopyranosyl-(1$\rightarrow$4)-O-$\beta$-D-galactopyranosyl-(1$\rightarrow$4)-D-glucose.

2. An alkylated oligosaccharide and the acetyl derivative of the same, wherein the hydrogen atom of the hydroxy group at the 1-position in the terminal sugar moiety of an oligosaccharide, in which glucose moieties are $\beta(1\rightarrow3)$-glycoside-linked, is substituted by an alkyl group having a linear or branched chain.

3. An alkylated oligosaccharide and the acetyl derivative of the same, wherein the hydrogen atom of the hydroxy group at the 1-position in the terminal sugar moiety of an oligosaccharide in which galactose is β(1→4)-glycoside-linked at the 4-position in the galactose moiety of lactose and in which galactose moieties are β(1→4)-glycoside-linked in succession to newly formed terminal galactose moieties, is substituted by an alkyl group having a linear or branched chain, with the exception of O-β-D-galactopyranosyl-(1→4)-O-β-D-galactopyranosyl-(1→4)-D-glucose.

4. An alkylated oligosaccharide and the acetyl derivative of the same as recited in claim 2, wherein the oligosaccharide has the glucose moieties in which sugar residues are in the range of 3 to 20.

5. An alkylated oligosaccharide and the acetyl derivative of the same as recited in claim 3, wherein the oligosaccharide has the galactose moieties in which sugar residues are in the range of 2 to 19 excluding the terminal glucose.

6. An alkylated oligosaccharide and the acetyl derivative of the same as recited in any one of claims 1 to 5, wherein the alkyl group has a linear or branched chain having 22 or fewer carbon atoms.

7. A mixture including at least two compounds of the alkylated oligosaccharides and the acetyl derivatives of the same as in claim 1.

8. An acetyl derivative of an alkylated oligosaccharide, wherein the hydrogen atom of the hydroxy group at the 1-position in the terminal sugar moiety of an oligosaccharide in which glucose moieties are β(1→3)-glucoside-linked, or of an oligosaccharide in which galactose is β(1→4)-glycoside-linked at the 4-position in the galactose moiety of lactose and in which galactose moieties are β(1→4)-glycoside-linked in succession to the newly formed terminal galactose moieties, is substituted by an alkyl group having a linear or branched chain; and wherein the hydroxy groups excluding the 2-positional hydroxy group adjacent to the alkyl-ether-linking position in the terminal sugar moiety are acetylated.

9. A mixture including at least two compounds of the alkylated oligosaccharides and the acetyl derivatives of the same as recited in any one of claims 2–5, wherein the alkyl group has a linear or branched chain having 22 or fewer carbon atoms.

* * * * *